(12) United States Patent
Naka et al.

(10) Patent No.: US 6,325,975 B1
(45) Date of Patent: Dec. 4, 2001

(54) SUCTION GENERATING DEVICE AND SAMPLE ANALYSIS APPARATUS USING THE SAME

(75) Inventors: Michio Naka; Kouji Hirayama, both of Kyoto; Yoshihiko Higuchi; Masafumi Koike, both of Osaka; Hisashi Okuda, Kyoto, all of (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 09/137,169

(22) Filed: Aug. 20, 1998

(30) Foreign Application Priority Data

Aug. 27, 1997 (JP) .................................................. 9-231506

(51) Int. Cl.[7] .................................................. G01N 21/00
(52) U.S. Cl. .............................. 422/61; 422/50; 422/55; 422/58; 422/68.1; 422/60
(58) Field of Search ...................... 422/68.1, 81, 82, 422/61, 60, 50, 58, 55; 436/48, 49, 44

(56) References Cited

U.S. PATENT DOCUMENTS

| 3,620,676 | 11/1971 | Davis ...................... 422/57 |
| 4,065,263 | 12/1977 | Woodbridge, III ............ 422/57 |
| 4,088,448 | 5/1978 | Lilja et al. ............... 422/102 |
| 4,195,526 | 4/1980 | Amos et al. .............. 73/864.11 |
| 4,624,928 | 11/1986 | Qureshi .................. 436/179 |
| 4,650,662 | 3/1987 | Goldfinger et al. ......... 435/7.25 |
| 5,120,420 | 6/1992 | Nankai et al. ............. 204/403 |
| 5,188,455 | * 2/1993 | Hammerstedt ............. 366/150 |
| 5,192,415 | 3/1993 | Yoshioka et al. ........... 204/403 |
| 5,262,037 | 11/1993 | Markle et al. ............. 204/415 |
| 5,264,103 | 11/1993 | Yoshioka et al. ........... 204/403 |
| 5,310,471 | 5/1994 | Markle et al. ............. 204/415 |
| 5,354,448 | 10/1994 | Markle et al. ............. 204/415 |
| 5,387,327 | 2/1995 | Khan ..................... 204/403 |
| 5,469,846 | 11/1995 | Khan ..................... 600/347 |
| 5,575,895 | 11/1996 | Ikeda et al. .............. 204/403 |
| 5,582,697 | 12/1996 | Ikeda et al. .............. 204/403 |
| 6,001,307 | * 12/1999 | Naka et al. ............... 422/81 |

FOREIGN PATENT DOCUMENTS

| 2 090 659 | 7/1982 | (GB) . |
| 1-291153 | 11/1989 | (JP) . |
| 4-188065 | 7/1992 | (JP) . |
| 7-167820 | 7/1995 | (JP) . |
| 8-114539 | 5/1996 | (JP) . |
| WO 96/00614 | 1/1996 | (WO) . |

* cited by examiner

*Primary Examiner*—Jill Warden
*Assistant Examiner*—Dwayne K. Handy
(74) *Attorney, Agent, or Firm*—Merchant & Gould P.C.

(57) ABSTRACT

A suction generating device for a sample analysis device is provided. The device comprises four parts, namely, a cover plate 61, a middle plate 62, a bottom plate 63 and an operation plate 64. A protruding portion 642 for compressing the suction generating chamber is formed in an approximately center portion on the lower side of the operation plate 64, a protruding portion 641 for operation is formed in an approximately center portion on the upper side of the operation plate 64. A cavity 631 for inserting the sample analysis device therein is formed in an approximately center portion in the bottom plate 63, and a hole 632 for light irradiation is punched in a determined portion in the cavity 631. A concave portion 623 for fitting the operation plate 64 therein is formed in the middle plate 62, and a window section 621 is formed in the center of the concave portion 623 to let the lower protruding portion 642 on the operation plate 64 protrude therethrough. A window section 611 is formed in the cover plate 61 to let the upper protruding portion 641 on the operation plate 64 protrude therethrough.

9 Claims, 10 Drawing Sheets

SUCTION GENERATING DEVICE AND SAMPLE ANALYSIS APPARATUS USING THE SAME

FIELD OF THE INVENTION

The present invention relates to a suction generating device for developing suction in a sample analysis device, in which the suction is utilized for forced-sucking.

BACKGROUND OF THE INVENTION

There are various types of samples in the field of analytical chemistry, and particularly in the medical field, body fluids such as blood, urine, spinal fluid, saliva, and the like, are important subjects for analysis. A need has arisen for analyzing such samples in large amounts and collectively.

In order to meet this need, a sample analysis device, having a reagent film previously impregnated with a reagent and stuck on a strip, has been developed and used. In such a device, the reagent film is supplied with a sample such as blood, and the sample is allowed to react with the reagent to generate a pigment, which develops a color in the reagent film, and then the degree of the color is analyzed by an optical measuring apparatus such as a densitometer. By using this device, operations for preparing a reagent and allowing the reagent to react with the sample can be simplified, so that the whole analysis operation can be converted into a routine exercise.

In such a sample analysis device, examples of methods for supplying the reagent film with a sample include a method utilizing capillarity, spotting, dipping, and the like. Among these methods, methods utilzing capillarity have been most commonly used. Because it is required to intercept external light during optical measuring, the sample supplying portion and the analysis section must be positioned at a considerable distance from one another when the device is set in an optical measuring apparatus. Therefore, the sample must be moved in the device, capillarity being used as the means for moving the sample. Examples of devices utilizing capillarity are disclosed in Japanese Published Unexamined Patent Application No. Hei 4-188065 and Japanese Published Unexamined Patent Application No. Sho 57-132900.

Figure 10:
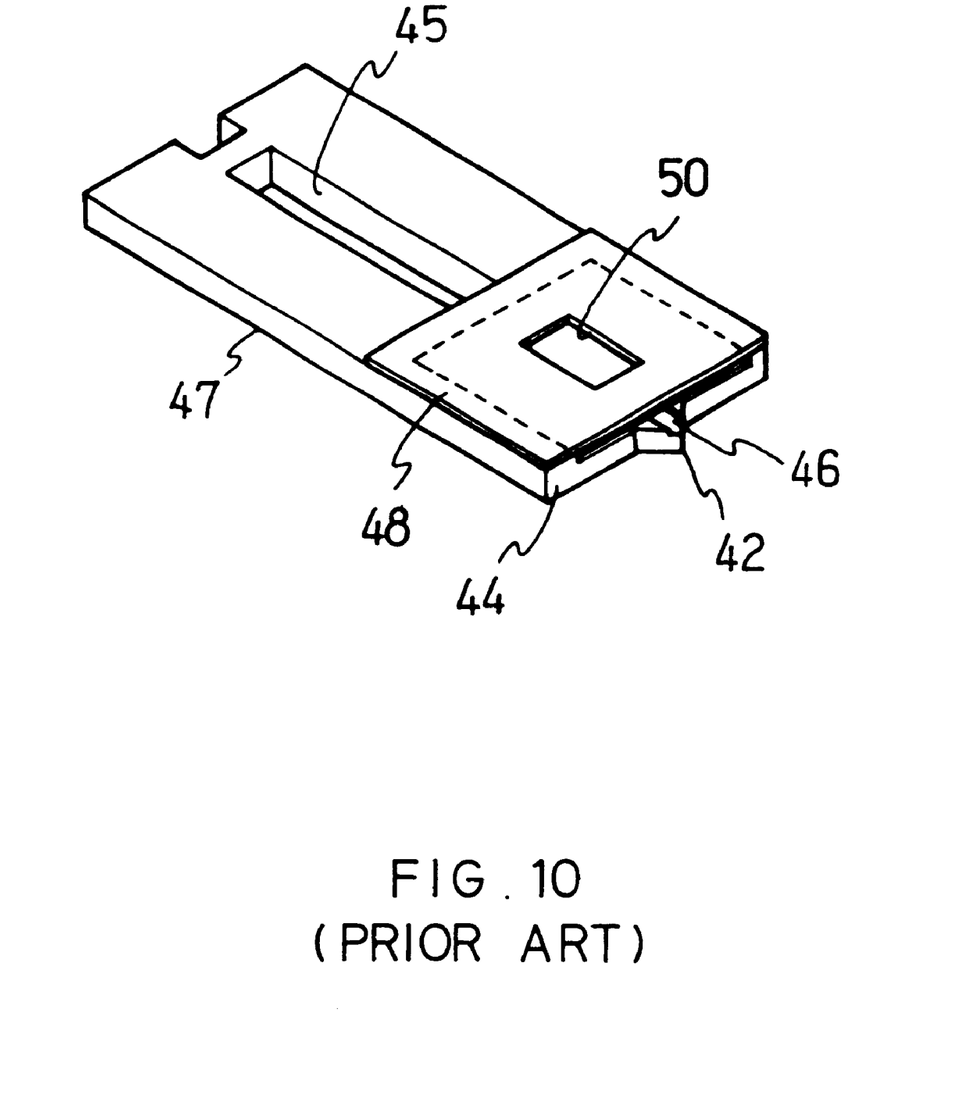
FIG. 10 is a perspective view of a conventional sample analysis device.

FIG. 10 shows one example of a sample analysis device utilizing capillarity. As shown in the drawing, the device has a triangular shaped sampling point 42 protruding from an approximately center portion of the front face 44 of a transparent base member 47 made of acrylic resin, a groove 46 extending from the sampling point 42 toward the back portion of the base member 47, and a slot 45 formed as an extension of the groove. Furthermore, a reagent film 48 is stuck on the upper face of the base member 47 on the side of the front face 44 so that it may cover the groove 46. The structure of the reagent film 48 is determined as appropriate depending on the type of the sample. For example, when analyzing plasma components of blood, the reagent film used comprises a filtration layer, a reagent layer, a transparent protective layer, and an opaque protective layer, which are laminated in this order from the bottom, and in which an observation window 50 for entering light is formed in an approximately center portion in the opaque protective layer.

Analysis using this device may be carried out as in the following steps. First, a drop of blood is obtained from a subject and brought into contact with the sampling point 42. Then, the blood is drawn into the groove 46 by capillarity and the whole groove is filled with the blood. When the blood permeates into the reagent film 48 covering the upper portion of the groove 46, first erythrocytes are removed by the filtration layer, and plasma components reach the reagent layer and are allowed to react with the reagent to generate a pigment, which develops a color in the reagent layer. In this state, the device is set in an optical measuring apparatus such as a densitometer, where the degree of the color developed in the reagent layer is measured by irradiating light through the observation window 50.

However, in using a device utilizing capillarity, there are problems as described below.

First, because a capillary channel needs to be continuously filled with a sample in order to cause capillarity, the sample must be provided in a larger amount than is required in analysis. In addition, because it takes some time to introduce the sample by capillarity, measuring cannot be carried out quickly. Furthermore, in body fluids such as blood, there are individual differences in properties such as viscosity, which affect capillarity, so that time required for introducing the sample into the analysis section or the like cannot be fixed. As a result, the time required for analysis, including the time for reaction with a reagent, is difficult to be fixed, and also an error might be caused in the analysis results. Furthermore, since the drawing force by capillarity is very weak, it is easily affected by gravity. Therefore, when introducing a sample, the inclination of the device has to be restricted, and also the structure of the optical measuring apparatus used is limited. Furthermore, the sample supplying portion and the analysis section cannot be positioned at a distance from each other because of the weakness of the drawing force by capillarity, therefore, in an optical measuring apparatus, possibilities of contamination of the measuring apparatus during introduction of a sample, or influence of external light, cannot be completely eliminated.

On the other hand, the spotting method for supplying samples has the disadvantage in that, when using blood as the sample, the sampling spot is limited to a fingertip, and sampling from an ear or the abdomen is difficult to perform.

SUMMARY OF THE INVENTION

It is an object of the present invention to provide a suction generating device for developing suction in a sample analysis device, which utilizes the suction to achieve rapid and precise analysis of a small amount of sample.

Viewed from a first aspect, the present invention provides a first suction generating device for developing suction in a suction generating chamber in a sample analysis device, said sample analysis device comprising a suction generating chamber having elasticity, a drawing channel in communication with the suction generating chamber, an analysis section formed in a certain position in the drawing channel, and a suction opening formed at the end of the drawing channel, said suction generating device comprising a compressor for compressing the suction generating chamber and a releaser for releasing the chamber from compression.

Previously, the applicant has separately filed applications for inventions related to a sample analysis device utilizing forced suction (Japanese Patent Application No. Hei 8-107310, Japanese Patent Application No. Hei 8-236131, and Japanese Patent Application No. Hei 9-102204). By using these devices, a small amount of sample can be analyzed rapidly and precisely. The applicant has developed the suction generating device of the present invention in order to improve the operational performance of a forced suction type sample analysis device, and further expand the range of its application. In a general method of using the sample analysis device, first, a sample needs to be drawn into the sample a analysis device by suction developed by a manual operation, and then the device is set in a testing machine, so that complex operation is often required. Therefore, the present invention achieves automation for generating suction by providing a device comprising a compressor for compressing the suction generating chamber and a releasor for releasing the chamber from the compression. That is, the suction generating chamber is automatically compressed simply by setting the sample analysis device in the device of the present invention. Therefore, if the device of the present invention is installed in a testing apparatus or the like, the analysis operation can be simplified In a preferred embodiment of the present invention, the suction generating device further comprises a cavity into which is inserted a sample analysis device and which holds said sample analysis device therein, and a protruding portion capable of compressing the suction generating chamber as the sample analysis device is inserted into the cavity, the protruding portion being movable, such that the suction generating chamber can be released from compression by moving the protruding portion.

In this embodiment, when the sample analysis device is inserted into the cavity, the suction generating chamber is automatically compressed by the protruding portion. In this state, the suction opening of the sample analysis device is brought into contact with a sample such as blood, and thereafter, by moving the protruding portion, the suction generating chamber is released from compression, and suction is developed as the chamber returns to its original shape. This suction transfers the sample into the analysis section of the device. Then, the sample is analyzed by an optical means such as densitometry.

In an alternative embodiment of the invention, the suction generating device is applied for developing suction in a sample analysis device, in which an air vent hole is formed in a suction generating chamber. The process for inserting the sample analysis device into the suction generating device includes two stages. This suction generating device further comprises a first protruding portion capable of compressing the suction generating chamber in a first stage of insertion, and a second protruding portion capable of dosing the air vent hole in the suction generating chamber in a second stage of insertion, during which the sample analysis device is inserted deeper into the cavity so that the suction generating chamber is released from compression.

As stated above, this suction generating device is used with a sample analysis device having an air vent hole formed in the suction generating chamber. This device is used, for example, in the following process. First, a sample is brought into contact with the suction opening of the sample analysis device and is held in a portion near the opening in the drawing channel by capillarity. Then, in a first stage, the sample analysis device is inserted into the cavity of the suction generating device so that the suction generating chamber is compressed by the first protruding portion. During this compression, the air contained in the suction generating chamber is discharged through the air vent hole, so that the sample held in the portion near the opening in the drawing channel cannot be pushed out. Then, in a second stage, the sample analysis device is inserted deeper into the cavity so that the chamber is released from the compression by the first protruding portion, while the air vent hole is dosed with the second protruding portion. As a result, suction is developed as the suction generating chamber returns to its original shape, thereby transferring the sample into the analysis section. Then, as mentioned above, the sample is analyzed by an optical means or the like.

By using the above device, a sample can be moved simply by inserting the sample analysis device into the suction generating device, so that operation of sampling is simplified. Furthermore, the operation of holding the sample in a portion near the opening in the drawing channel in the sample analysis device may be performed after the analysis device has been inserted in the suction generating device in the first stage.

Furthermore, in the above-mentioned device, the two-stage insertion can be carried out in one step, that is, the sample is continuously transferred into the analysis section in one inserting operation.

The present invention also provides a further device for developing suction in the suction generating tube in a sample analysis device, which sample analysis device comprises a suction generating tube having elasticity, a drawing channel in communication with the suction generating tube, an analysis section formed in a certain position in the drawing channel, and a suction opening formed at the end of the drawing channel, one end of the suction generating tube being open and the other end communicating with the drawing channel, and the suction generating tube being arranged in such a manner that its open end is turned toward the end of the sample analysis device having the suction opening. This further device comprises a cavity into which is inserted the sample analysis device and which holds the sample analysis device therein, and a protruding portion provided at a certain position inside the cavity which is capable of sequentially deforming the suction generating tube to generate suction as the sample analysis device is inserted into the cavity.

The device is for use with a sample analysis device having a suction generating tube as a means for developing suction. The suction generating tube develops suction as it is sequentially deformed. The device is used, for example, as follows: First, the suction opening in the sample analysis device is brought into contact with a sample which is held in a portion near the opening in the drawing channel by capillarity. Then, the suction generating tube is sequentially deformed by the protruding portion to develop suction as the sample analysis device is inserted into the cavity, thereby transferring the sample into the analysis section. Then, the sample is analyzed by an optical means or the like.

The present invention also provides a sample analysis apparatus comprising a suction generating device in accordance with the present invention and a means for analyzing a sample. This sample analysis apparatus may comprise conventionally known components of the invention in addition to the suction generating device of the invention. Examples of means for analyzing a sample include an optical analysis means comprising a light irradiating section and a light detecting section, an electrical analysis means comprising an electric signal generating means and an electric signal detecting means, or the like. These means can be also any conventionally known means.

BRIEF DESCRIPTION OF THE DRAWINGS

Some preferred embodiments of the invention will now be described by way of example only and with reference to the accompanying drawings in which:

FIG. 1 (A) is a plan view of one example of a sample analysis device, and FIG. 1 (B) shows a cross-sectional view taken along the line III—III of FIG. 1 (A);

FIG. 4 (A) is a plan view of the suction generating device of FIG. 3, and FIG. 4 (B) is a cross-sectional view taken along the line I—I of FIG. 4 (A);

FIG. 5 (A) is a plan view of a sample analysis device in a condition in which a sample is held in the liquid pooling portion in the device.

PREFERRED EMBODIMENT OF THE INVENTION

EXAMPLE 1

Figure 1A:
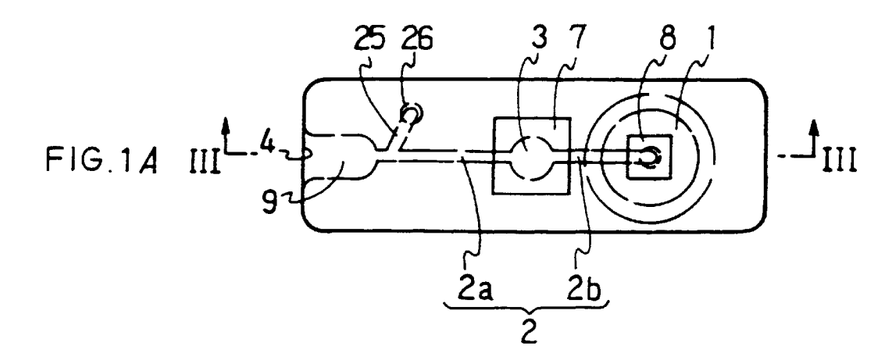
Figure 1B:
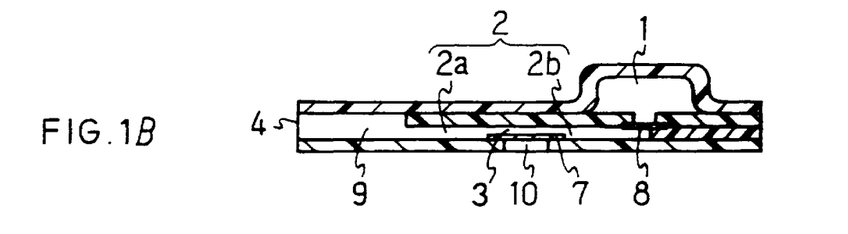

Firstly, FIG. 1 shows an example of a sample analysis device usable with the first and second embodiments of suction generating devices of the present invention. FIG. 1 (A) is a plan view of the sample analysis device, and FIG. 1 (B) is a cross-sectional view taken along the line III—III of FIG. 1 (A). As shown in the drawings, the sample analysis device is formed by laminating a plurality of films, and the body is approximately rectangular plate shaped.

In this sample analysis device, a suction generating chamber 1 is formed as a protrusion in an end side portion of the approximately rectangular plate shaped body (right side in the drawing), and a drawing channel 2 extends from a position below the suction generating chamber 1 toward the end (the other end) opposite to the suction generating chamber 1 in the approximately rectangular plate shaped body. An analysis section 3 is formed in a certain position in the drawing channel 2, and the end of the drawing channel 2 communicates with a suction opening 4 formed at the other end of the approximately rectangular plate shaped body through a liquid pooling portion 9. A window 10 is formed under the analysis section 3. The window 10 may be formed as needed. For example, when glucose oxidase (GOD) is used as a reagent, because this reagent requires oxygen for color development, a window should be formed for supplying oxygen. However, except in such a case, if the portion of the film corresponding to the analysis section 3 is transparent so that light may be admitted into the analysis section 3, such a window is not required. Furthermore, a reagent film 7 impregnated with a reagent is placed below the analysis section 3 in such a manner so that it covers the window 10. Furthermore, a gas-permeable liquid-impermeable stopper 8 is formed in a certain position between the suction generating chamber 1 and the analysis section 3 in that part 2b of the drawing channel 2 on the side of the suction generating chamber 1. The gas-permeable liquid-impermeable stopper 8 is formed by placing a hydrophobic porous film in a given position in the drawing channel 2b.

Furthermore, an air vent passage 25 branches from a certain position between the liquid pooling section 9 and the analysis section 3 in the section 2a of the drawing channel 2, and its end 26 opens to the outside of the body. Thus, as its ends are both open, the air vent passage 25 develops capillarity.

Furthermore, the size of the cross section of the air vent passage 25 is smaller than that of the passage of the liquid pooling portion 9, thus liquid flow resistance in the air vent passage 25 is larger than in the liquid pooling portion 9. In particular, the width of the liquid pooling portion 9 is about four times those of the drawing channel 2 and the air vent passage 25, and the thickness of the liquid pooling portion 9 is about twice those of the drawing channel 2 and the air vent passage 25.

Figure 2:
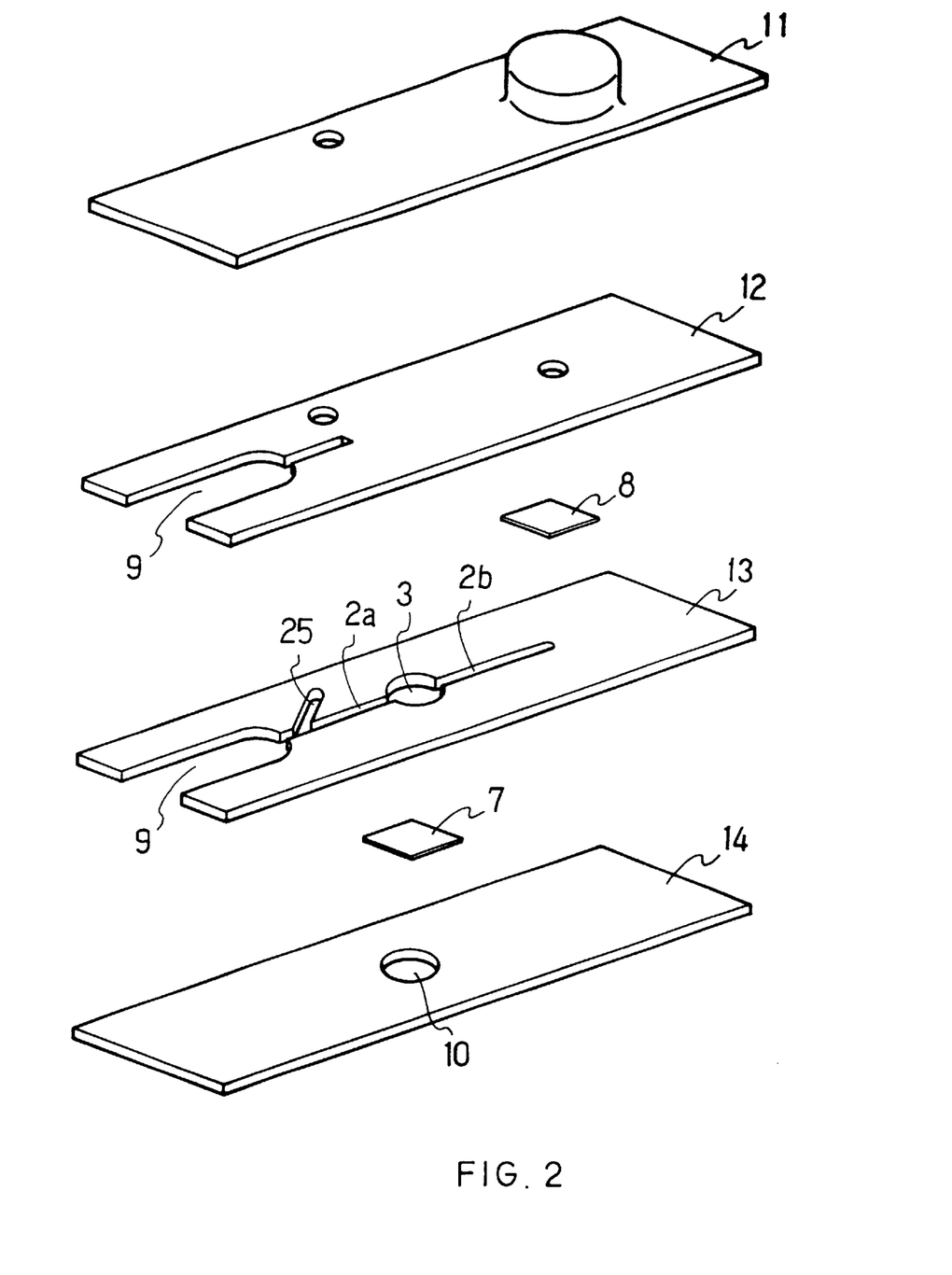
FIG. 2 is an exploded perspective view of the sample analysis device of FIG. 1.

Such a sample analysis device comprising laminated films can be produced, for example, by laminating films 11, 12, 13 and 14 which are formed into various shapes with the reagent film 7 and the hydrophobic porous film 8 therebetween as shown in FIG. 2.

The film 14 is prepared to form the back side of the sample analysis device, and the window 10 is formed therein. In the film 13, cut-out portions for forming the liquid pooling portion 9, the air vent passage 25, the analysis section 3 and the drawing channel 2 are formed. The film 12 is prepared to ensure the thickness of the liquid pooling portion 9 (the size of the cross section of the passage), and a cut-out portion for forming the liquid pooling portion 9, a circular cut-out portion for making the end of the air vent channel 25 open, and a circular cut-out portion for leading the drawing channel 2b to the suction generating chamber 1 are formed in the film. In the film 11, an approximately cylindrical convex portion for forming the suction generating chamber 1 is formed as a protrusion, and a circular cut-out portion for making the end of the air vent passage 25 open is also formed.

Then, the reagent film 7 is placed between the film 14 and the film 13 in a position to form the analysis section 3, and the hydrophobic porous film 8 is placed between the film 13 and the film 12 in a position to be a certain place in the drawing channel 2b, and in this state, the four films 14, 13, 12 and 11 are laminated in this order from the bottom and integrated together, so that the sample analysis device shown in FIG. 1 can be produced.

An example of the above-mentioned hydrophobic porous film is hydrophobic resin porous film, and particular examples are polyethylene porous film, polypropylene porous film, polytetrafluoroethylene (PTFE) porous film, and the like. Examples of suitable hydrophobic resin porous film in the present invention include Celgard (product name; produced by Hoechst Celanese Co., Ltd.), and Hipore (product name; produced by Asahi Chemical Industry Co., Ltd.). The average diameter of the pores in the hydrophobic resin porous film is usually from 0.1 to 1 $\mu$m, preferably from 0.3 to 0.7 $\mu$m. Furthermore, the thickness of the hydrophobic resin porous film is usually from 10 to 100 $\mu$m. Such a hydrophobic resin porous film can be produced, for example, by forming a film using said hydrophobic resin and then orienting the film either uniaxially or biaxially.

The reagent film 7 is prepared by impregnating a film with a reagent, and the type of the reagent is selected as appropriate depending on the type of the object to be analyzed. The structure of the reagent film is also determined as appropriate depending on the type of the object for analysis. For example, when plasma components of blood are to be analyzed, the reagent film used usually comprises a filtration layer for separating etythrocytes, a reagent layer impregnated with a reagent, and a base material, which are laminated in this order. Then, the reagent film 7 is arranged in the analysis section 3 in such a manner that the filtration layer can contact with blood (a liquid sample). Furthermore, conventionally known materials can be used for the respective layers in the reagent film.

When the sample analysis device is produced, the films may be integrated together by bonding the films to each other with an adhesive, or by laminating by pressing or heating.

Furthermore, examples of the materials for the films constituting the sample analysis device include polyethylene, polyethylene terephthalate (PET), polystyrene, polyvinyl chloride, and the like. Among these examples, PET is preferably used because of its good processibility.

The dimensions of the sample analysis device shown in FIG. 1 are as follows. The overall size of the device is usually 15 to 60 mm in length, 5 to 20 mm in width and 1 to 3 mm in thickness. Furthermore, the size of the suction generating chamber 1 is usually 3 to 15 mm in diameter and 0.5 to 3 mm in height. The size of the drawing channel 2 is usually 10 to 40 mm in overall length, 0.5 to 2 mm in width and 0.1 to 0.5 mm in thickness; and usually, the drawing channel 2a is 5 to 30 mm in length, and the drawing channel 2b is 5 to 30 mm in length. Furthermore, the size of the analysis section 3 is usually 2 to 10 mm in diameter and 0.1 to 1 mm in height. The size of the liquid pooling section 9 is usually 2 to 10 mm in length, 2 to 10 mm in width, and 0.2 to 1 mm in thickness. The size of the air vent passage 25 is usually 2 to 10 mm in overall length, 0.5 to 2 mm in width and 0.1 to 0.5 mm in thickness; and the opening thereof is usually 0.5 to 5 mm in diameter. The size of the suction opening 4 is usually 2 to 10 mm in width and 0.2 to 1 mm in thickness.

Figure 3:
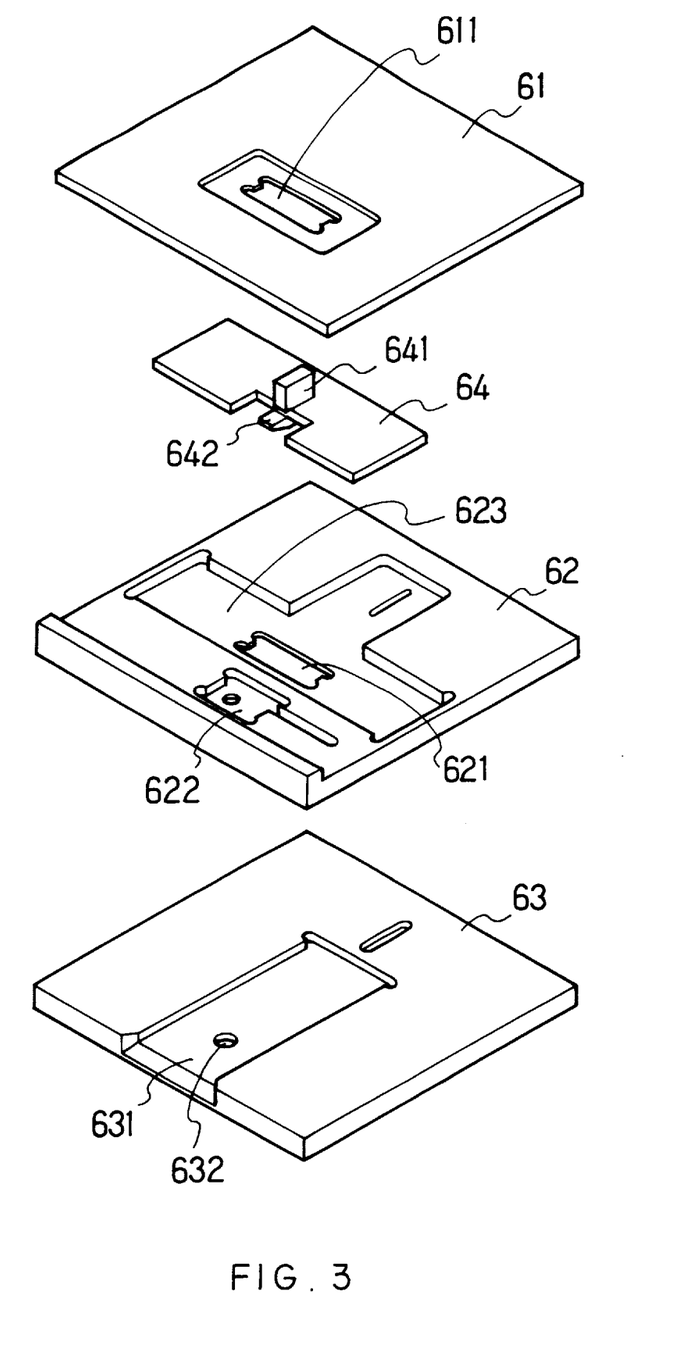
FIG. 3 is an exploded perspective view of one embodiment of a suction generating device according to the present invention.
Figure 4A:
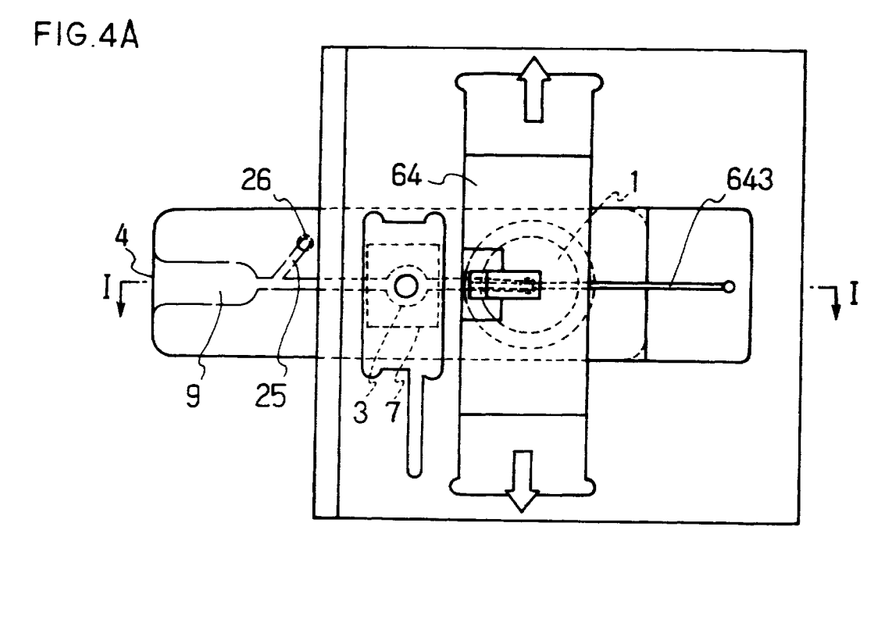
Figure 4B:
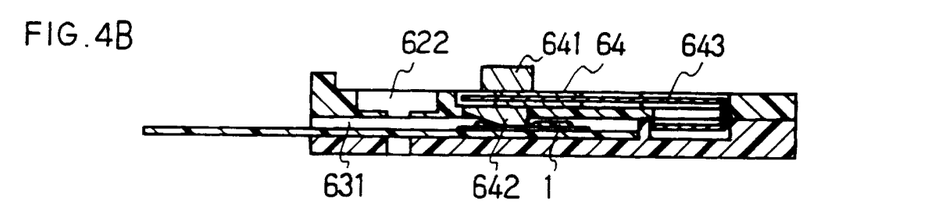

Next, an example of an embodiment of a suction generating device according to the present invention for developing suction in the suction generating chamber 1 of the above sample analysis device will be illustrated referring to FIGS. 3 and 4.

FIG. 3 is an exploded perspective view of the above-mentioned device. As shown in the drawing, this device comprises four parts, namely, a cover plate 61, a middle plate 62, a bottom plate 63 and an operation plate 64. A protruding portion 642 for compressing the suction generating chamber is formed in an approximately center portion on the lower side of the operation plate 64, and a protruding portion 641 (a finger grip) for operation is formed in an approximately center portion on the upper side of the operation plate 64. A cavity 631 for inserting the sample analysis device therein is formed in an approximately center portion in the bottom plate 63, and a hole 632 for light irradiation is punched in a determined portion in the cavity 631. The hole 632 is formed in a position that will correspond to the analysis section 3 when the sample analysis device is inserted into the cavity. A concave portion 623 for fitting the operation plate 64 therein is formed in the middle plate 62, and a window section 621 is formed in the center portion of the concave portion 623 to let the lower protruding portion 642 on the operation plate 64 protrude therethrough. Furthermore, an open section 622 for placing a detector such as an optical sensor is formed in the middle plate 62. A window section 611 is formed in the cover plate 61 to let the upper protruding portion 641 on the operation plate 64 protrude therethrough.

The dimensions of this device are determined as appropriate depending on the size of the sample analysis device used. For example, when it is applied to the above-mentioned sample analysis device, the dimensions are as follows: First, the size of the bottom plate 63 is usually 2 to 10 mm in thickness; the cavity 631 is usually 5 to 20 mm in width, 1 to 5 mm in depth and 20 to 60 mm in length; and the size of the hole 632 is usually 2 to 10 mm in diameter. The size of the operation plate 64 is usually 15 to 50 mm in length, 5 to 20 mm in width and 1 to 10 mm in thickness; and usually, the upper protruding portion 641 is 2 to 5 mm in height, and the lower protruding portion 642 is 1 to 5 mm in height. The size of the middle plate 62 is usually 20 to 60 mm in length, 20 to 60 mm in width and 1 to 5 mm in thickness; the size of the concave portion for positioning the operation plate 64 is usually 20 to 70 mm in length and 5 to 20 mm in width; the size of the window section 621 formed in the concave portion is usually 10 to 30 mm in length and 3 to 10 mm in width. The size of the cover plate 61 is usually 20 to 60 mm in length, 20 to 60 mm in width and 1 to 5 mm in thickness; and the size of the window section 611 for letting the upper protruding portion 641 on the operation plate 64 protrude therethrough is usually 10 to 30 mm in length and 3 to 10 mm in width.

The materials for forming this device are not particularly limited, and for example, the operation plate 64 is made of metals such as aluminum, iron, brass, or the like. Examples of the materials used for forming other parts include acrylonitrile-styrene-butadiene copolymer (ABS resin), polyacetal resin, acrylic resin, vinyl chloride resin, and the like.

FIG. 4 shows the assembly of this device, in which the sample analysis device (for reference, see FIG. 1) is inserted. FIG. 4 (A) is a plan view of the device, and FIG. 4(B) is a cross-sectional view taken along the line I—I of FIG. 4(A). In FIG. 4, the same parts are designated by the same signs as in FIG. 1 and FIG. 3. Furthermore, 643 refers to a wire type spring for positioning the lower protruding portion 642 formed on the operation plate 64 continuously in the center of the cavity. In this device, as shown by the cross-sectional view in FIG. 4 (B), when the sample analysis device is inserted into the cavity 631, the suction generating chamber 1 is compressed with the protruding portion 642. Furthermore, as shown in FIG. 4 (A), the operation plate 64 is capable of sliding in vertical direction relative to the cavity 631 (i.e. upwards or downwards direction as shown with the arrows in the drawing), so that the lower protruding portion 642 can be moved.

Figure 5A:
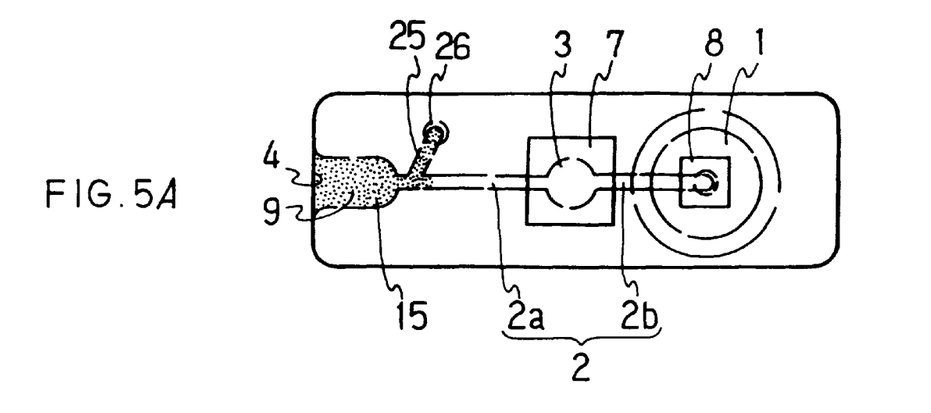
Figure 5B:
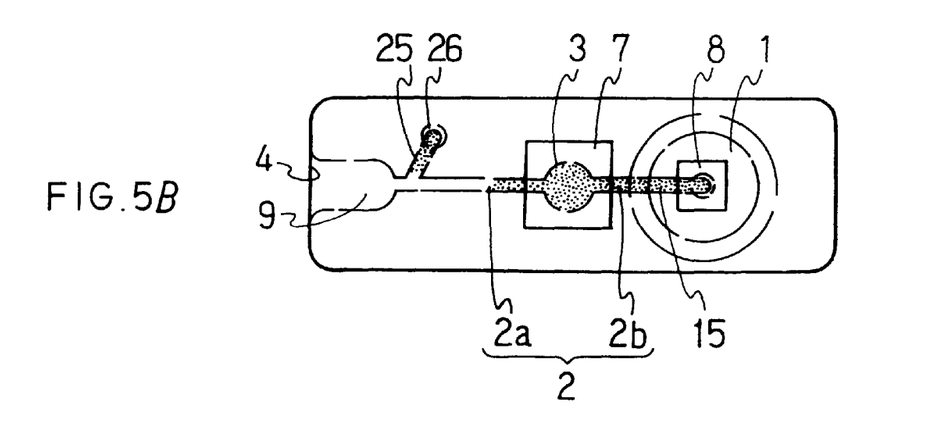
FIG. 5(B) is a plan view of the device in a condition in which the sample is moved into the analysis section.

Next, sampling and analyzing a sample using the above device and the sample analysis device (for reference, see FIG. 1) will be described referring to FIGS. 4 and 5. Also, in FIG. 5, the same parts are designated with the same signs as in FIG. 1.

As shown in FIG. 4 (3), as the sample analysis device is inserted and set in the cavity 631 of this device, the suction generating chamber 1 is compressed with the lower protruding portion 642. In this state, the suction opening 4 of the sample analysis device is brought into contact with a sample 15. Then, as shown in FIG. 5(A), the sample 15 is drawn into the opening 4 by capillarity developed by the air vent passage 25 and held in the liquid pooling portion 9. Furthermore, as shown in FIG. 4(A), if the operation plate 64 is slid in either direction as shown by the arrows, the lower protruding portion 642 is moved, so that the suction generating chamber 1 is released from compression. As a result, suction is developed as the suction generating chamber 1 returns to its original shape, and as shown in FIG. 5 (B), the sample 15 held in the liquid pooling portion 9 is introduced into the analysis section 3 through the drawing channel 2a by the suction. The introduction of the sample into the analysis section 3 occurs within a very short period of time compared to introduction by capillarity, and moreover, it is hardly affected by the properties of the sample such as viscosity. Furthermore, in this drawing process, because the relative liquid flow resistance in the liquid pooling portion 9 and the air vent passage 25 is adjusted as described above, a part of the sample 15 remains in the air vent passage 25 as shown in the drawing, so that inclusion of air can be prevented. Furthermore, even if excess suction is developed, because the gas-permeable liquid-impermeable stopper 8 is formed, the sample 15 cannot flow into the suction generating chamber 1, so that introduction of the sample into the analysis section 3 is ensured. Furthermore, in the analysis section 3, reaction occurs between the sample 15 and the reagent in the reagent film 7 to generate a pigment, which develops a color in the reagent film 7. Then, light is irradiated through the window 10 in the lower surface of the sample analysis device, and in case of the above-mentioned densitometry, reflected light is detected at the detecting section and the degree of the color is measured. Furthermore, in this measurement, if the whole analysis section 3 is transparent and the reagent film 7 is also transparent, analysis can be performed with transmitted light as well. Furthermore, as the sample analysis device is pulled out of the device, the operation plate 64 is automatically returned to its original position by the wire type spring 643.

EXAMPLE 2

Figure 6:
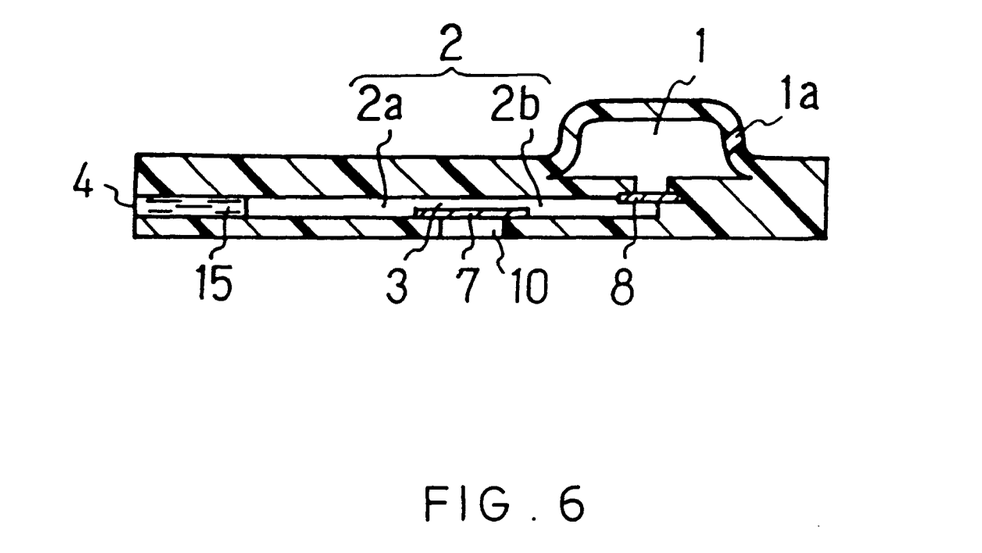
FIG. 6 is a cross-sectional view of another example of a sample analysis device.

Next, FIG. 6 shows a cross-sectional view illustrating an example of a sample analysis device, in which an air vent hole is formed in the suction generating chamber.

As shown in FIG. 6, the sample analysis device has the same structure as the sample analysis device described in Example 1 shown in FIG. 1, except that an air vent hole 1a is formed in the device. Therefore, the same parts are designated with the same reference numerals. The size of the air vent hole 1a is usually in the range of 0.1 to 5 mm in diameter.

Next, FIG. 7 shows cross-sectional views illustrating an example of the structure of a second embodiment of the present invention which is used with the sample analysis device, and an example of its use.

Figure 7A:
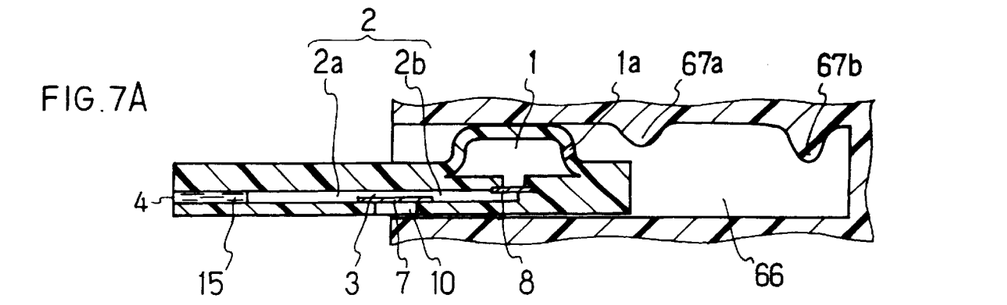
FIGS. 7(A)–7(D) are cross-sectional views showing another embodiment of a suction generating device of the present invention and its method of use.

As shown in the drawing, the device has a cavity 66, and two protruding portions 67a and 67b formed in certain positions inside the cavity. The size of the device varies depending on the type of the sample analysis device used. For example, when it is applied to the sample analysis device shown in FIG. 6, the size of the cavity 66 is usually 20 to 60 mm in length, 2 to 10 mm in height and 5 to 20 mm in width; and usually, the protruding portion 67a is 0.5 to 9 mm in height, and the protruding portion 67b is 0.5 to 9 mm in height. Furthermore, the materials for forming the device are the same as mentioned above.

Figure 7B:
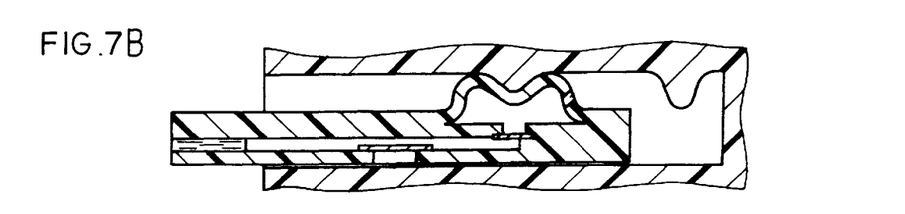
Figure 7C:
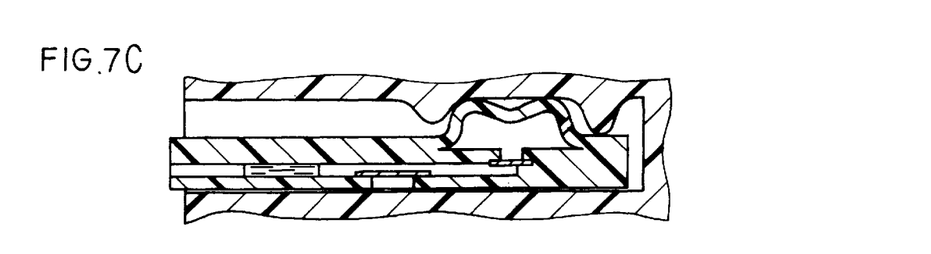
Figure 7D:
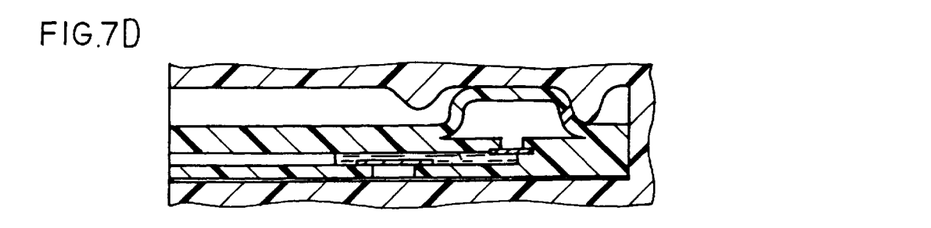

The device is used, for example, as follows: First, the suction opening 4 of the sample analysis device is brought into contact with a sample 15, and the sample 15 is held in the liquid pooling portion 9. Then, in a first stage of insertion, the sample analysis device is inserted into the cavity 66 as shown in FIG. 7(B) so that the suction generating chamber is compressed by the protruding portion 67a. During this stage, because the air contained in the suction generating chamber 1 escapes from the air vent hole 1a, the sample is not discharged from the opening 4 by the pressure of the air from the suction generating chamber 1. Then, in a second stage of insertion, the sample analysis device is inserted deeper into the cavity 66 so that the chamber is released from the compression by the protruding portion 67a (FIG. 7 (C)), while the air vent hole 1a is closed with the protruding portion 67b (FIG. 7 (D)). During this stage, suction is developed as the compressed suction generating chamber is released to return to its original shape, thereby moving the sample 15 through the drawing channel 2 and into the analysis section 3 (FIG. 7 (D)). Even if the air vent is dosed (FIG. 7 (C)), the suction force that is developed in the suction generating chamber displays its effect in the drawing channel, thereby drawing the sample through the channel. The subsequent operation is the same as described above. Furthermore, the two-stage process of the insertion of the sample analysis device into the cavity of this suction generating device can be carried out either in one step or in two steps. If the sample analysis device is inserted in two steps, the process becomes as follows: In the first step, the insertion is continued until the suction generating chamber is compressed, and then it is stopped for a while, and in this state, the opening is brought into contact with a sample so that the sample is drawn into the liquid pooling portion by capillarity and is held therein, and then, in the second step, the device is inserted deeper into the cavity and suction is generated, thereby transferring the sample into the analysis section.

EXAMPLE 3

Next, a further embodiment of a device according to the present invention will be described. First, an example of the sample analysis device for use with this device is shown in cross-sectional view in FIG. 8.

Figure 8:
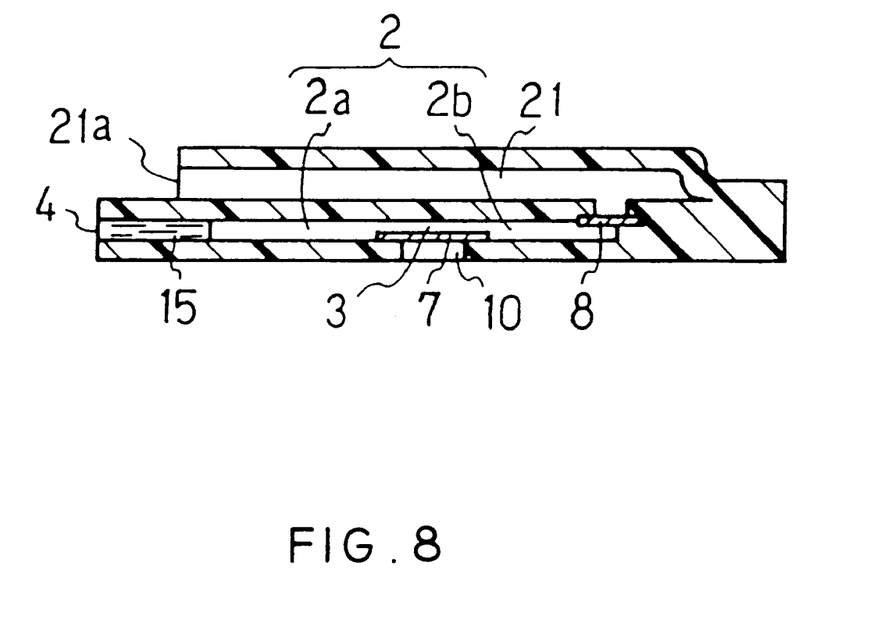
FIG. 8 is a cross-sectional view of still another example of a sample analysis device.

As shown in FIG. 8, the sample analysis device is the same as the device shown in FIG. 1 except that it has a suction generating tube 21 in place of a suction generating chamber, so that the same parts are designated by the same reference numerals. The suction generating tube 21 can be formed, for example, by positioning a resin sheet, which is bent in a manner so that its cross section in the longitudinal direction becomes an approximately reverse U-shape, on the body of the sample analysis device. In this case, one end of the suction generating tube communicates with the drawing channel 2 through the gas-permeable liquid-impermeable stopper 8, and the other end of the tube is open (opening 21a). The size of the suction generating tube is usually as follows: The thickness of the sheet is in the range of 0.01 to 2 mm, the height inside the tube is in the range of 0.5 to 5 mm, the width inside the tube is in the range of 1 to 10 mm, and the length of the tube is in the range of 5 to 30 mm. The suction generating tube 21 is preferably formed in such a manner that it does not overlap with the drawing channel 2, the analysis section 3, or the like. This is because, in order to develop suction in suction generating tube 21, it is required to draw the tube through by pressing. However, this pressing might cause deformation of the drawing channel, or the like. Examples of the materials for forming the resin sheet include soft vinyl chloride resin, soft silicon resin, natural rubber, and the like. Furthermore, the shape of the cross section of the suction generating tube in the longitudinal direction is not limited to the reverse U-shape, and for example, it may be rectangular, or the like.

Next, examples of the structure and use of this device with the sample analysis device are shown in the cross-sectional views in FIG. 9.

Figure 9A:
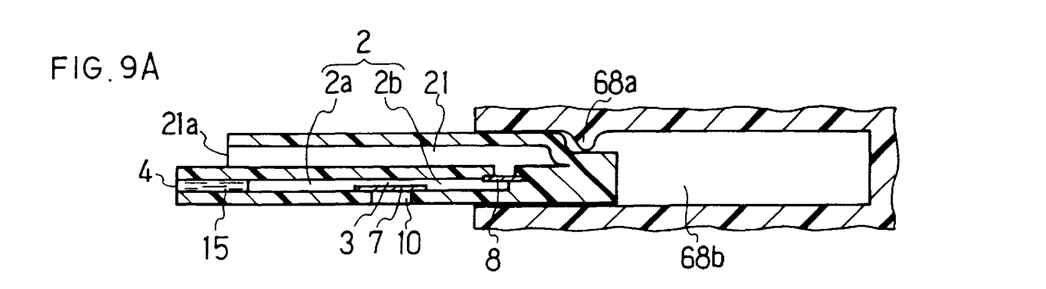
FIGS. 9(A)–9(B) are cross-sectional views showing still another embodiment of the suction generating device of the present invention and its method of use.

As shown in the drawings, the device has a cavity 68b, and a protruding portion 68a formed near the opening of the cavity 68b. The size of the device varies depending on the type of the sample analysis device used. For example, if it is applied to the sample analysis device shown in FIG. 8, the size of the cavity 68b is usually 20 to 60 mm in length, 2 to 10 mm in height, and 5 to 20 mm in width; and the protruding portion 68a is usually 0.5 to 9 mm in height. Furthermore, the materials for forming the device are the same as mentioned above.

Figure 9B:
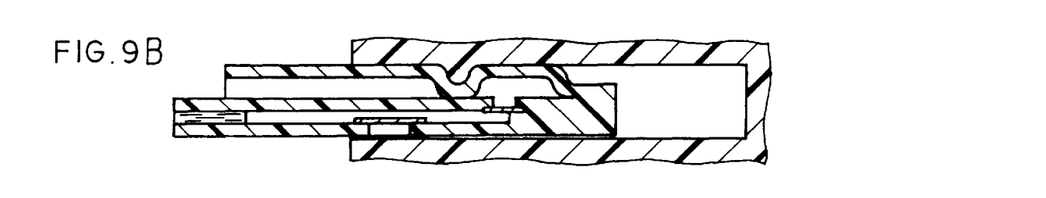
Figure 9C:
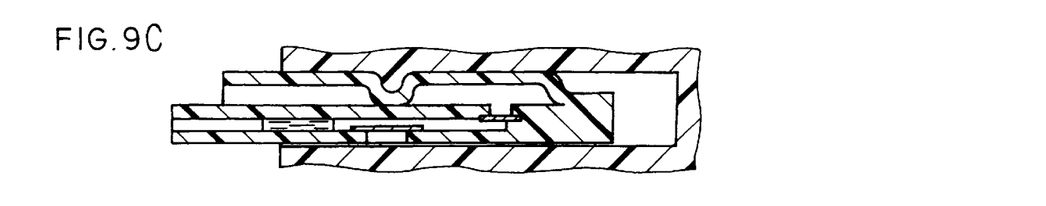
Figure 9D:
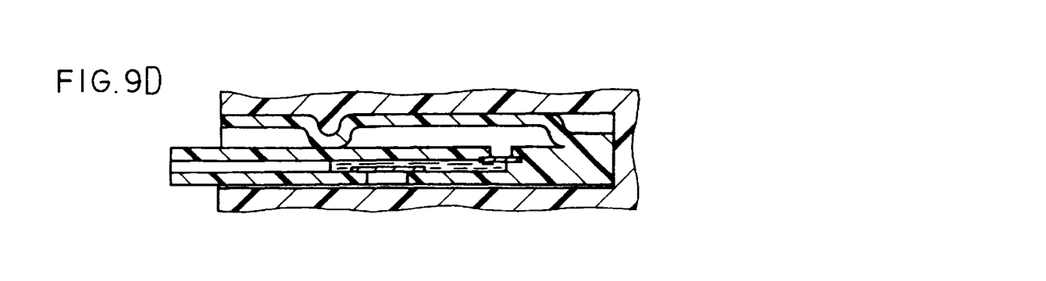

This device is used, for example, as follows: First, the suction opening 4 of the sample analysis device is brought into contact with a sample 15, and the sample 15 is held in the liquid pooling portion 9. Then, as shown in FIG. 9(B), as the sample analysis device is inserted into the cavity 68b, the suction generating tube 21 is pressed in the portion in communication with the drawing channel 2. Then, as shown in FIGS. 9 (B), (C) and (D) in order, as the sample analysis device is inserted deeper into the cavity, the suction generating tube 21 is sequentially deformed by the protruding portion 68a to develop suction, and the sample 15 is thereby moved through the drawing channel 2 and introduced into the analysis section 3. The subsequent analysis operation is the same as in the above-mentioned Examples.

Finally, it is understood that the invention may be embodied in other specific forms without departing from the spirit or essential characteristics thereof. The embodiments disclosed in this application are to be considered in all respects as illustrative and not restrictive, so that the scope of the invention being indicated by the appended claims rather than by the foregoing description, and all changes which come within the meaning and range of equivalency of the claims are intended to be embraced therein.

What is claimed is:

1. A sample analyzing assembly comprising a sample analysis device and a suction generating device for developing suction in the suction generating chamber in a sample analysis device, the sample analysis device comprising a suction generating chamber having elasticity, a drawing channel in communication with the suction generating chamber, an analysis section formed in the drawing channel, and a suction opening formed at the end of the drawing channel, said suction generating device comprising a compressor for compressing the suction generating chamber and a releaser for releasing the chamber from compression.

2. The sample analyzing assembly according to claim 1, which further comprises a cavity into which is inserted a sample analysis device and which holds said sample analysis device therein, and a protruding portion capable of compressing the suction generating chamber as the sample analysis device is inserted into the cavity, the protruding portion being movable such that the suction generating chamber can be released from compression by moving the protruding portion.

3. The sample analyzing assembly according to claim 2, in which after moving the protruding portion to release the suction generating chamber from compression, the protruding portion automatically returns to its original position.

4. The sample analyzing assembly according to claim 3, which further comprises a spring in communication with the protruding portion, and the spring does not develop its elasticity before the suction generating chamber is released from compression, and when the protruding portion is moved to release the suction generating chamber from compression, the spring develops its elasticity, which enables the protruding portion to return to its original position after the chamber is released from compression.

5. The sample analyzing assembly according to claim 2, in which a window for transmitting light irradiated from the outside is formed in the cavity.

6. The sample analyzing assembly according to claim 1 for developing suction in a sample analysis device with a suction generating chamber having an air vent hole formed therein, which further comprises a cavity into which the sample analysis device is inserted, the insertion including two stages, and which further comprises a first protruding portion capable of compressing the suction generating chamber as the sample analysis device is inserted into the cavity in a first stage, and a second protruding portion capable of closing the air vent hole in the suction generating chamber as the sample analysis device is inserted deeper into the cavity in a second stage, during which the suction generating chamber is released from compression.

7. A sample analyzing assembly comprising a sample analysis device and a suction generating device for developing suction in the suction generating tube in a sample analysis device, which sample analysis device comprising a suction generating tube having elasticity, a drawing channel in communication with the suction generating tube, an analysis section formed in the drawing channel, and a suction opening formed at the end of the drawing channel, one end of the suction generating tube being open and the other end communicating with the drawing channel, and the suction generating tube being arranged in such a manner that its open end is turned towards the end of the sample analysis device having the suction opening, and which suction generating device comprises a cavity into which is inserted the sample analysis device and which holds the sample analysis device therein, and a protruding portion provided inside the cavity which is capable of sequentially deforming the suction generating tube to generate suction as the sample analysis device is inserted into the cavity.

8. A sample analyzing assembly according to claim 1, wherein the sample analyzing assembly has overall dimensions of 15 to 60 mm in length, 5 to 20 mm in width, and 1 to 3 mm in thickness.

9. A sample analyzing assembly according to claim 1, wherein the sample analyzing assembly is formed by laminating a plurality of films and is approximately rectangular plate shaped.

* * * * *